United States Patent [19]

Edwards

[11] Patent Number: 4,934,935
[45] Date of Patent: Jun. 19, 1990

[54] DENTAL PROSTHESES

[76] Inventor: Barry N. Edwards, 71 Marchmont St., London, United Kingdom, WCIN 1AP

[21] Appl. No.: 209,482
[22] PCT Filed: Oct. 21, 1987
[86] PCT No.: PCT/GB87/00742
  § 371 Date: Jul. 1, 1988
  § 102(e) Date: Jul. 1, 1988
[87] PCT Pub. No.: WO88/03007
  PCT Pub. Date: May 5, 1988

[30] Foreign Application Priority Data

Oct. 21, 1986 [GB] United Kingdom ............... 8625174

[51] Int. Cl.⁵ ............................................. A61C 8/00
[52] U.S. Cl. .................................. 433/174; 433/173
[58] Field of Search ............. 433/173, 174, 175, 176, 433/201.1

[56] References Cited

U.S. PATENT DOCUMENTS

| | | | |
|---|---|---|---|
| 3,499,222 | 3/1970 | Linkow et al. | 433/174 |
| 3,732,621 | 5/1973 | Bostrom | 433/174 |
| 4,180,910 | 1/1980 | Straumann et al. | 433/173 |
| 4,253,833 | 3/1981 | Edelman | 433/173 |
| 4,531,915 | 7/1985 | Tatum, Jr. | 433/173 |
| 4,636,216 | 1/1987 | Tatum | 433/173 |
| 4,645,453 | 2/1987 | Niznick | 433/173 |
| 4,738,623 | 4/1988 | Driskell | 433/173 |
| 4,793,808 | 12/1988 | Kirsch | 433/173 |

FOREIGN PATENT DOCUMENTS

| | | | |
|---|---|---|---|
| 0037864 | 10/1981 | European Pat. Off. | 433/172 |
| 0038897 | 11/1981 | European Pat. Off. | |
| 2103092 | 2/1983 | United Kingdom | 433/173 |

*Primary Examiner*—John J. Wilson
*Attorney, Agent, or Firm*—Dennison, Meserole, Pollack & Scheiner

[57] ABSTRACT

An anchor (1) adapted to be implanted for osseo integration by the known and perfected surgical techniques, together with an intermediate transmucosal spacer member (2) for mounting a dental prosthesis (4) using an interposed post (3), the combination being such that the transmucosal spacer member and the post mounted thereon when installed, constitute in effect an axially offset extension of the anchor, the angle (37) of the offset of the post axis being variable and selectable, and the offset of the extension being adjustable as to its orientation in azimuth relative to the implanted anchor (1), prior to permanent or semi-permanent fixing, by relative rotation of parts at a bonded and preferably keyed plug and socket type connection (21) between the intermediate transmucosal spacer member (2) and one end of the anchor (1).

31 Claims, 5 Drawing Sheets

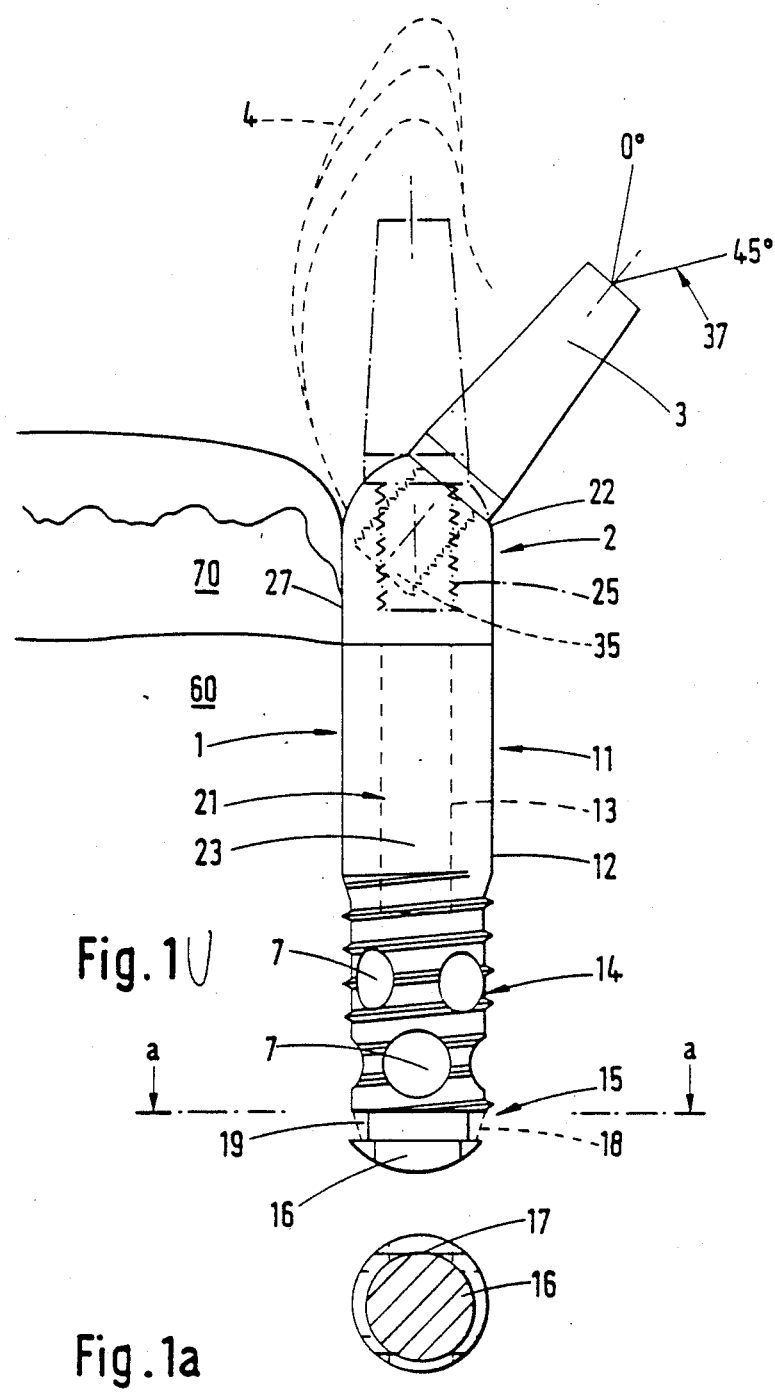

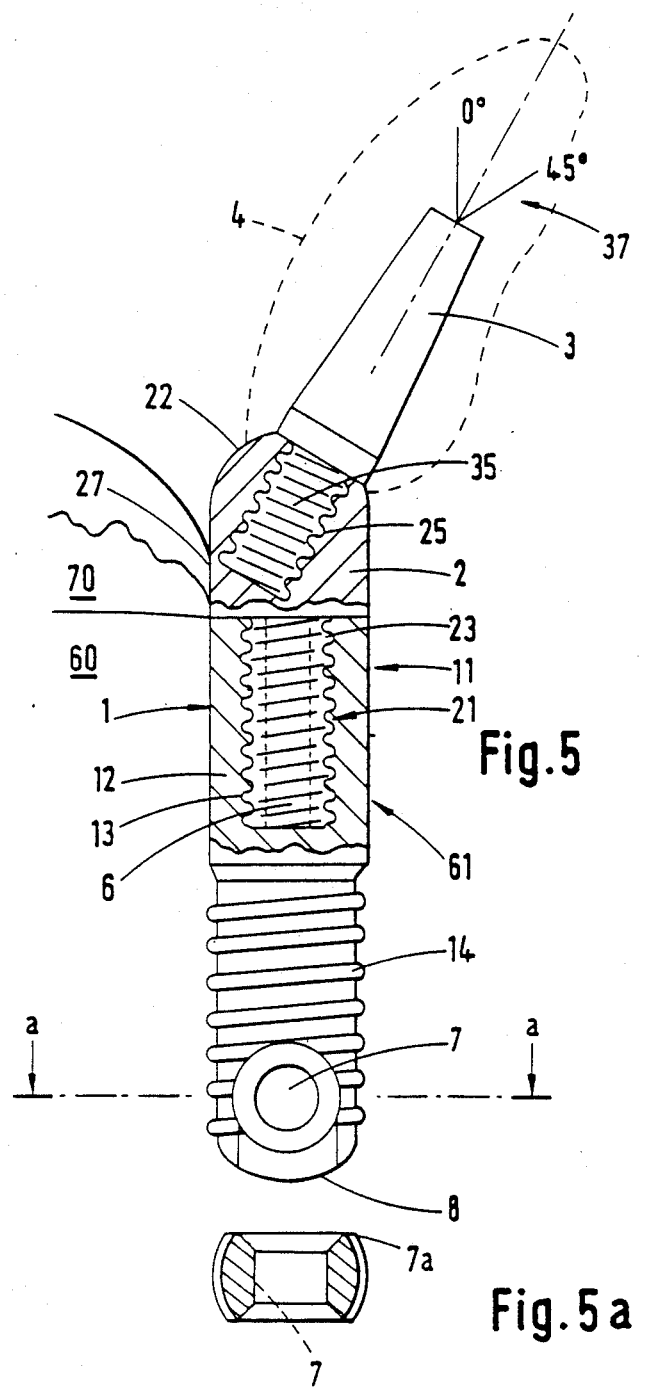

DENTAL PROSTHESES

BACKGROUND OF THE INVENTION

This invention relates to prostheses mounted upon anchors which are implanted in bone, and for use in dental surgery.

For some years, it has been known to implant in the bone, an anchor to which may be attached a dental prosthesis, which latter may be a single crown or a set of crowns may be secured to a plurality of such implanted anchors. This technique has become practical firstly, because of the realisation that titanium, or high titanium alloy, is a suitable material to employ for the anchor, being non-reactive with bone and other body tissue or fluid; and secondly, and more importantly, because an efficacious surgical technique has been developed during recent years for implanting such anchors.

In particular, efficacious surgical techniques of implantation and prosthesis have been developed which have recently been described in—Tissue Integrated prosthesis; Osseo-integration in Clinical Dentistry—Edited by Per-Ingvar Branemark—Quintessence publishing Co Inc. Chicago, 1985.

These techniques have as salient characteristics (a) that the implant is made with such care and precision as to ensure that trauma to the bone is minimised; and (b) that after initial placing of the implant, the implant is left relatively undisturbed for a period of about six months before it is subjected to loading, and in particular before any prosthesis is attached to it During this "unloaded" period, healing and repair of the bone takes place and also the bone will, to a significant extent, integrate with the implanted anchor, the latter being suitably shaped such as to augment the structural integrity of the anchorage when such integration with the bone is accomplished Various types of titanium anchor are in use. These in general, comprise small plugs which although of sometimes quite complex shape in detail, are generally cylindrical, ranging in length from say 7 to 20 mm and ranging in diameter from say 3 to 7 mm. Some of these anchors have, over all or part of their outer surface, annular ribs or screw threads which may be self tapping threads. Some anchors have, at their foot ends, hollow cores and there may be also transverse through holes; it being intended that during osseo integration during the healing period after initial implantation, bone should reform and move into the hollow cavities of the anchor.

In U.S. Pat. No. 3,499,222, published 10th Mar. 1970, there are described examples of known implant anchors, which are generally cylindrical; which may be externally threaded; and which may have hollow cores and through holes in the walls defining these cores. In U.S. Pat. No. 4,180,910, published 1st Jan. 1980, further anchors for dental implant are described. These are of titanium and are of the kind with apertured hollow cores shaped and intended for re-entry of the bone into the hollow cavities of the anchor during the healing period after initial implantation.

The prosthesis is secured to these anchors by small screw threaded bolts, and usually a transmucosal spacer member is interposed between the prosthesis and the anchor, it being generally the case that the head of the anchor is level with the periphery of the bone, and hence beneath the level of the surface of the mucosa or gum tissue of the patient.

Such a transmucosal spacer element may be secured to the anchor by a small screw-threaded bolt engaging in a preformed threaded axial socket in the head end of the anchor, and, in turn, the prosthesis may be secured to the transmucosal spacer member, it may be by a small screw threaded bolt or in some cases, by a press-fit ball and socket connection which may be cemented by an adhesive.

With an anchor of the type heretofore known, in addition to having at its head end an axial hole threaded to receive fixture bolts, the head end of the anchor may be appropriately shaped so that it can be engaged by a spanner or key. For example it may be provided with outwardly facing spanner flats for receiving an open ended spanner; or it may have a hexagonal socket to receive a small Allen type key. When such a hexagonal socket is provided, it will be located at the outer extremity of the threaded axial hole intended to receive the fixture bolt; if spanner flats are provided these are located adjacent the extremity of the head end of the anchor.

As stated above the prosthesis is usually secured to a transmucosal spacer member which in turn is secured to an implanted anchor. However the known systems are unsatisfactory in a number of respects. This is the case mainly because it is generally difficult to locate and dispose the implanted anchor so that it is not only adequately supported by regrown bone, but also may readily receive its intended attachments. In the case of a plurality of implanted inserts, the surgeon attempts to obtain parallelism for all the implanted anchors; this is difficult to achieve. Also the main requirement governing the procedure for initial implanting is that there should be caused minimal trauma, both to the bone and to other tissue etc; and this often mitigates against optimal location and disposition from other points of view. Here it should be mentioned that the shape and disposition of the eventual prosthesis is governed to a great extent by the requirements and physiology of the particular patient being treated. And in short, it is difficult to match optimal anchor location with the various other requirements.

Accordingly in the known implant systems and procedures, some degree of adjustability or adaptation has been provided so that the various and often conflicting requirments of oral bone anchor implant surgery can be met.

For example it has been proposed that the transmucosal spacer employed between the prosthesis and the anchor should be either bendable or otherwise deformable into the shape required, both as to its orientation in azimuth relative to the implanted anchor and as to the angle of inclination relative to the axis of the anchor of its region remote from the anchor; or the required shape is achieved in that a temporary transmucosal spacer is first inserted, then deformed into the shape required, and then removed and used as a model for a permanent transmucosal spacer. For example the deformed temporary transmucosal spacer may be used to make a mould for casting a permanent transmucosal spacer having inherently the final shape desired.

These procedures in turn involve disadvantages. If a permanent transmucosal spacer is deformed there is risk of undue stress being caused either to the bone, or to the implanted anchor, or to the transmucosal spacer itself. If the proceedure of using a temporary transmucosal spacer as a model is employed, there will be a delay in treatment which will adversely affect the patient.

SUMMARY OF THE INVENTION

One object of the present invention is to provide alternative viable devices, procedures and systems which incorporate anchors which can be implanted for osseo integration using the same surgical techniques developed by Branemark et al as referred to at the outset, but which are efficaciously adaptable to match the various and often conflicting requirements of implant surgery, and by which some of the disadvantages of the prior devices are reduced or avoided.

This invention starts out from the combination of a prosthesis (which may be a single crown or a mounted set of crowns), a post for mounting the prosthesis, an intermediate transmucosal spacer member which in turn mounts the post, and an anchor to a head of which the intermediate transmucosal spacer member is connected and which anchor is itself intended and adapted to be implanted e.g. by the surgical technique known from Branemark et al) in bone for osseo integration therewith.

The combination of these elements according to one aspect of this invention is characterised in that the intermediate transmucosal spacer member is joined to the head end of the anchor by means including an initially releasable plug and socket type connection, the post for mounting the prosthesis when connected to the intermediate transmucosal spacer member, extending away from the intermediate transmucosal spacer member in a direction which is offset at a predetermined angle from the axis of the anchor, the orientation in azimuth relative to the anchor, of said intermediate transmucosal spacer member with said post secured to it, being adjustable as and when the plug and socket connection between the intermediate transmucosal spacer member and the anchor is being made, the plug being at least initially, rotatable in the socket, after which the transmucosal spacer member is held secured to the anchor by bonding or cementing of the plug in the socket so that the orientation in azimuth of the transmucosal spacer member relative to the anchor is thereafter substantially fixed.

The intention is that once the transmucosal spacer member has been fixed to the anchor these two parts should remain generally undisturbed in the patient's jaw substantially covered by mucosal tissue. Accordingly and preferably, the intermediate transmucosal spacer member has a generally hemispherically domed head adapted to lie beneath or at the level of the mucosa, and beneath this and at its opposite end will be the said plug: this plug being in the form of an elongated spigot which is insertable into the socket in the anchor, the latter being buried well below the mucosa. The socket will be a preformed socket leading axially into the anchor from the head of the latter.

According to an important preferred feature of the invention, the plug and the socket, which may have substantially the same axial lengths, will each have corresponding respective keying means whereby, the orientation of the intermediate transmucosal spacer member in azimuth relative to the implanted anchor having first been adjusted by rotation of the plug in the socket the application of a bonding or cementing agent between the plug and the socket is effective both to clamp the anchor in the socket and to interact with the keying means of these two parts. Thereafter relative rotation between these two parts will be substantially prevented; that is except following the application of very substantial torque.

The keying means advantageously comprise formations such as flats or protuberances extending axially of the external surfaces of the plug and of the socket. In some embodiments, part of the length of the plug is hexagonal or splined and interengageable with a hexagonal or splined part of the length of the socket. The external surface of one or both of said plug and said socket may be formed with a screw-thread in addition to said keying means.

The domed head of the intermediate transmucosal spacer member will have one screw-threaded hole formed therein, and the post for mounting the prosthesis will have at its foot a threaded stud which can be screwed into the preformed hole in the intermediate transmucosal spacer member.

Such screw-threaded hole in the domed head of the intermediate transmucosal spacer member provided according to this aspect of the invention, will have an axis which is offset and inclined at a predetermined angle to the major axis of the intermediate transmucosal spacer member, (and from the axis of the anchor when the intermediate transmucosal spacer member is attached thereto), said predetermined angle being say between 5° and 45°.

A set of such intermediate transmucosal spacer members will be available for selection by the surgeon, each with holes of different offset angles, e.g. respectively differing by 5° such as in the series 5°, 10°, 15° . . . 35° 40° 45°.

According to an optional aspect of this invention, there will be provided in addition, as part of the set of such intermediate transmucosal spacer members available to the surgeon, one or more intermediate transmucosal spacer members with axially aligned, i.e. non-offset, tapped holes. It will be understood that in the particular case where there is a requirement to use a transmucosal spacer with an axially aligned tapped hole, this will occur when the implanted anchor is already substantially correctly aligned as desired, with other anchors or with the patient's existing teeth or prostheses: and in this case also there will be no need for adjustment of orientation in azimuth.

The post and the intermediate transmucosal spacer member are of the same material and may be of titanium or other inert material such as nylon, and the post will have the aforesaid threaded stud which can be screwed, into the preformed offset hole in the intermediate transmucosal spacer member. The prosthesis will be secured to this post.

At their junction beneath the mucosa, the plug having been inserted into the anchor socket, the intermediate transmucosal spacer member and the anchor will with advantage, have the same external cylindrical shape and diameter so that they will interfit with a minimal void. The cylindrical body portion of the intermediate transmucosal spacer member will advantageously have sufficient length such that when installed the domed head of the intermediate transmucosal spacer member will be approximately level with the surface of the patients mucosa or gum tissue.

The arrangement of the intermediate transmucosal spacer member with single preformed screw-threaded hole just described, can be efficiently acheived given good engineering, even in the case of anchors and intermediate transmucosal spacer members of small diameter, (that is to say with external diameters down to 2.5 mm), and where the space available is severely limited.

The sets of anchors available to the surgeon might be as follows:

| Diameter | Length |
| --- | --- |
| 2.5 mm | 10-20 mm |
| 3.5 mm | 7-20 mm |
| 4.5 mm | 4-20 mm |
| 5.5 mm | 4-20 mm |

And in such a set there will be intermediate transmucosal spacer members matching the anchors in diameter; and for each size there will be a plurality of intermediate transmucosal spacer members having preformed holes in their domed heads the holes of each being at different angle to the axis, selected from the range, say as follows:

0, 5, 10, 15, 20, 25, 30, 35, 40, and 45 degrees.

By these means there is achieved, without any bending or other deformation of parts in situ, such a combination of prosthesis, post, intermediate transmucosal spacer member and implanted anchor, that the transmucosal spacer member and the post mounted thereon when installed, constitute in effect an axially offset extension of the anchor, the angle of the offset having been selected, and the offset extension having been adjusted as to its orientation prior to fixing, by relative rotation of parts at the plug and socket type interconnection between the offset extension and the head of the anchor and this is acheived without delay being occasioned by need to make a permanent transmucosal spacer member from a model, as was required with some known systems above referred to.

According to a further aspect of this invention, there is provided a novel anchor which is suitably shaped and adapted to receive the intermediate transmucosal spacer member, discussed above; while it is also suitable to have other known devices mounted upon it.

BRIEF DESCRIPTION OF THE DRAWINGS

Various examples of such combinations are shown diagramatically and schematically in the accompanying drawings in which:

FIG. 1 shows an implanted anchor, an intermediate transmucosal spacer member, a post mounted thereon and also a crown mounted on the post.

FIG. 1a is a view in cross-section taken on the line a—a of FIG. 1.

FIG. 5 shows a further embodiment of an implanted anchor, an intermediate transmucosal spacer member, a post mounted thereon and also a crown mounted on the post.

FIG. 5a is a view in cross-section taken on the line a—a of FIG. 5.

Figure 3B:
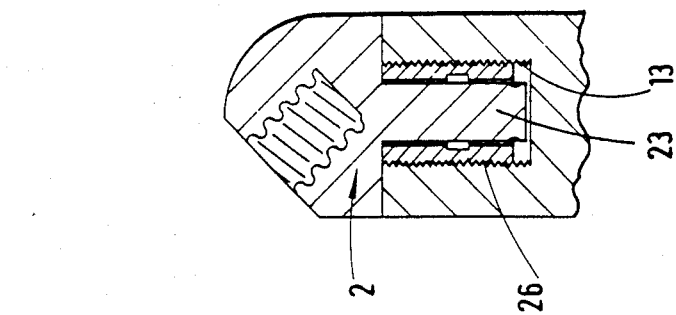
FIGS. 3a and 3b are views of an alternative arrangement.

Referring first to FIGS. 1 and 5, there is here shown an implanted anchor generally designated 1; an intermediate transmucosal spacer member generally designated 2 mounted on the anchor 1; a post generally designated 3 mounted on the intermediate transmucosal spacer member 2; and also a prosthesis generally designated 4, in this case a crown, is shown mounted on the post 3.

The anchor 1 whose shape and configuration will be discussed in more detail below, is intended to be, and is shown as, implanted in a patient's bone 60 surrounded by mucosa or gum tissue 70.

In the combination of these elements as shown in FIG. 1, the intermediate transmucosal spacer member 2 is joined to the head end 11 of the anchor 1 by means including a plug and socket connection generally designated 21. The connection 21 comprises a plug 23 on the member 2, which plug is insertable in a socket 13 preformed axially in one end of the anchor 1.

The post 3 extends away from the intermediate transmucosal spacer member 2 in a direction which is offset at a predetermined angle from the axis of the anchor 1, the orientation relative to the anchor 1, of said intermediate transmucosal spacer member 2 with said post 3 secured to it, being adjustable as and when the plug and socket connection 21 between the intermediate transmucosal spacer member 2 and the anchor 1 is being made, after which the transmucosal spacer member 2 is held secured to the anchor 1 for example by cementing or bonding.

The intermediate transmucosal spacer member 2 has a domed or hemispherical head 22 and opposite this the plug 23. This plug 23 is insertable into the a preformed socket 13 leading axially into the anchor 1 from the head of the latter and the plug 23 will be rotated In the socket 13 of the implanted anchor 1 to adjust the orientation in azimuth relative to the anchor of the intermediate transmucosal spacer member, after which the plug 23 may be fixed in the anchor socket 13 to prevent further relative movement.

Preferably, the plug and the socket of the connection 21 each have corresponding respective keying means whereby, the orientation of the intermediate transmucosal spacer member 2 in azimuth relative to the implanted anchor 1 having been adjusted by rotation of the plug 23 the socket 13, the application of a bonding or cementing agent between the plug and the socket is effective both to clamp the plug 23 in the socket 13 and to interact with the keying means of these two parts so as thereafter to prevent relative rotation between the two parts.

In the embodiment shown in FIG. 5, the keying means comprise a flat 6 extending axially of the external surfaces of the plug 23 and if the socket 13 is formed with walls having a plurality of flats: for example the walls may be generally hexagonal. Then when cement is applied there will be formed a key between one or more flats 6 on the plug and one or more flats on the socket walls. Instead of flats the keying means can be formed by protuberances or other formations which effect positive locking against rotation when cement or other bonding agent is applied.

In FIG. 5, the external surfaces of both of the plug and of the socket are formed with a screw-thread in addition to said keying means: and the plug and the socket have substantially the same axial length. Indeed the plug 23 may have various external shapings as shown in FIG. 6; but in each case it has at least one flat adapted when cement or other bonding agent is applied to key with at least one flat or protuberance formed in the socket of the anchor 1.

The domed head 22 of the intermediate transmucosal spacer member 2 has one screw-threaded hole 25 formed therein, the axis of this hole 25 being offset by a predetermined angle, from the major axis of the intermediate transmucosal spacer member, (and from the axis of the anchor when the intermediate transmucosal spacer member is attached thereto). and the post 3 for mounting the prosthesis 4 will have at its foot a threaded stud 35 which can be screwed into the preformed hole 25 in the intermediate transmucosal spacer member.

Such screw-threaded hole 25 in the domed head of the intermediate transmucosal spacer member 2 will have an axis which is inclined to the major axis of the intermediate transmucosal spacer member by an angle which is advantageously between 5° and 45°. A set of such intermediate transmucosal spacer members will be available for selection, each with holes of different offset angles, e.g. respectively differing by 5°; such as in the series 5°, 10°, 15°, 20°, 25°, 30°, 35°, 40° and 45°; these angles being indicated at 37 in FIGS. 1 and 5.

According to a further aspect of this invention, there will be provided in addition, as part of the set of such intermediate transmucosal spacer members available to the surgeon, one or more intermediate transmucosal spacer members with axially aligned. i.e. non-offset, tapped holes 25 in FIG. 1. It will be understood that in the particular case where there is a requirement to use a transmucosal spacer with an axially aligned tapped hole, this will occur when the implanted anchor is already correctly aligned as desired, and in this case also there will be no need for adjustment of orientation in azimuth, effected by rotation of parts at the plug and socket connection.

The post 3 to be secured to the intermediate transmucosal spacer member 2 may be of titanium or other inert material such as nylon, and it will have the aforesaid stud 35 which can be screwed into the preformed hole 25 in the intermediate transmucosal spacer member. The prosthesis 4 will be secured to this post which together with the intermediate transmucosal spacer member can be rotated relative to the implanted anchor 1.

12 represents a cylindrical shank portion of the anchor 1. The cylindrical body portion 27 of the intermediate transmucosal spacer member will have sufficient length such that when installed the domed head 22 of the intermediate transmucosal spacer member 2 will be approximately level with the surface of the patients mucosa or gum tissue. At their junction the intermediate transmucosal spacer member 2 and the anchor 1, advantageously, will have the same external cylindrical shape and diameter.

Figure 2:
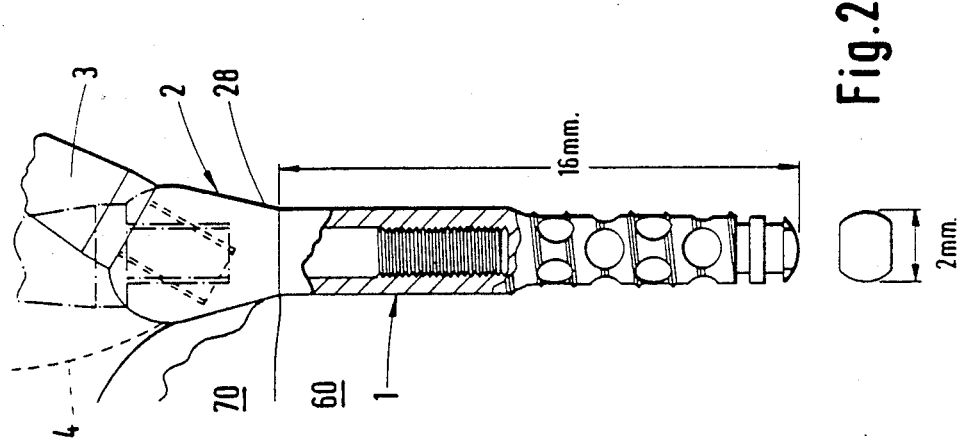
FIG. 2 shows a similar combination but which has a matching intermediate transmucosal spacer member and anchor which are of small diameter as compared with the combination of FIG. 1.

The arrangement of the intermediate transmucosal spacer member with a single preformed screw-threaded hole 25 just described, can be efficiently achieved given good engineering, even in the case of anchors and intermediate transmucosal spacer members of small diameter, (that is to say with external diameters down to 2.5 mm), and where the space available is severely limited. For example, and as shown in FIG. 2, the upper part of the anchor 1 can have a diameter of 2.5 mm while its threaded lower part may have a diameter of only 2.0 mm. In such a configuration space is extremely limited and in order to cater for this, the intermediate transmucosal spacer member 2 is, in these circumstances, afforded a larger diameter than that of the anchor 1; with the cylindrical body portion 27 of FIG. 1 being replaced by a tapered body portion 28 in FIG. 2.

Figure 3A:
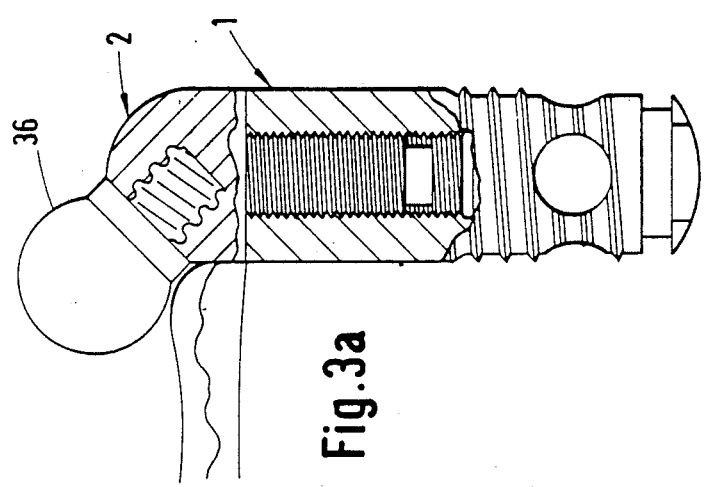

In the arrangement shown in FIG. 3a–3b, an externally threaded sleeve 26 is shown inserted beteen the plug 23 of the member 2 and the socket 13 of the anchor 1, this socket being correspondingly screw threaded. The plug 23 is as usual cemented in place after adjustment for orientation, but in this arrangement the member 2 can be detached from the anchor 1 by unscrewing should this become absolutely necessary. This arrangement is not suitable in small diameter systems.

The screwthreads on the outside of the sleeve 23 are preferably right handed, there being preferably, left handed screw threads on the stud 35 engaging in the tapped hole 25.

Also shown in FIG. 3a is a post 3 with a dome shaped head 36. Such a head which may be of titanium or nylon, is commonly employed in the art for securing by press-fit ball and socket type connection, a prosthesis for example in the form of a bridge. Such a bridge type prosthesis would in practice be so secured to a plurality of implanted anchors.

Figure 4:
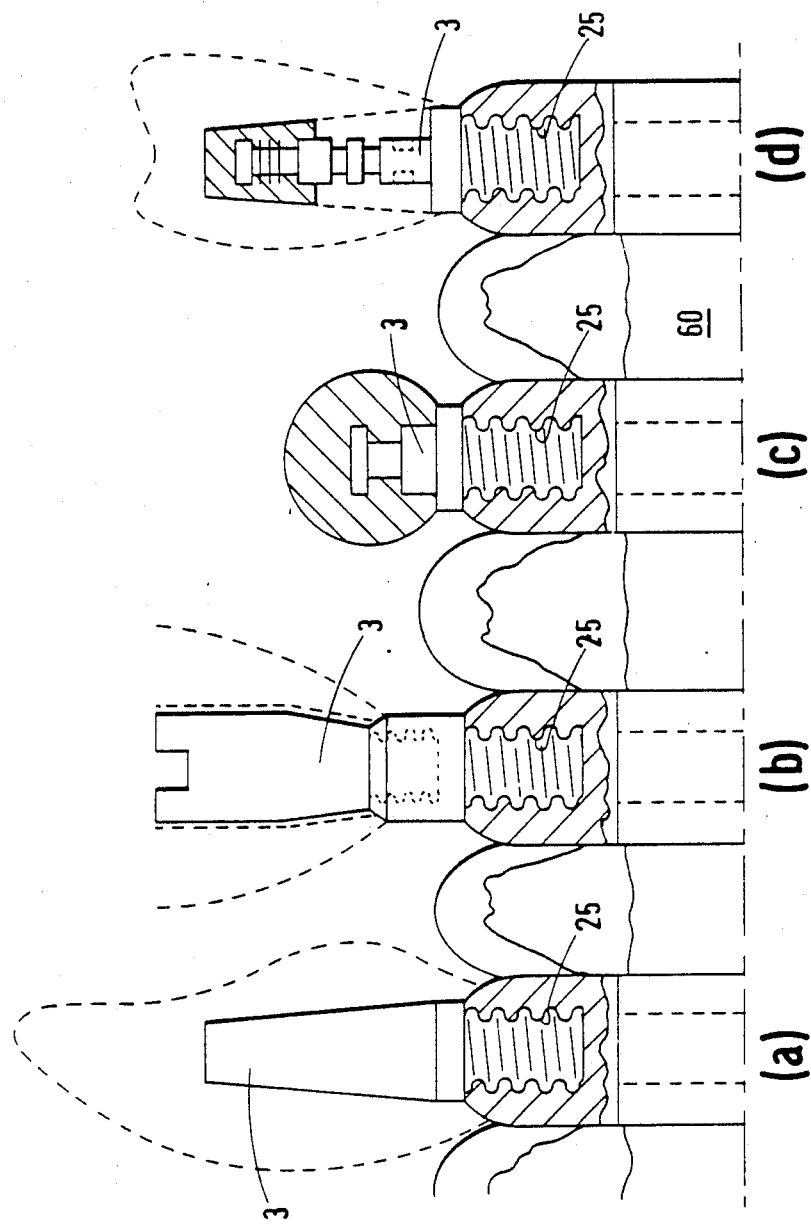
FIGS. 4a through 4d show an intermediate transmucosal spacer member surmounted by a post in alternative configurations.

Various other configurations for the post 3 are depicted in FIG. 4. In each case the arrangement permits an intermediate transmucosal spacer member 2 having a preformed threaded hole 25 of the required offset angle, to be selected to achieve the required offset angle for the post 3, while the desired orientation in azimuth relative to the implanted anchor 1, of the offset post 3, is achieved by rotation of the plug 23 of the intermediate transmucosal spacer member 2 in the socket 13 of the anchor 1 prior to permanent fixing.

According to a further aspect of this invention, there is provided a novel anchor which is suitably shaped and adapted to receive the intermediate transmucosal spacer member, discussed above; while it is also suitable to have other known devices mounted upon it.

Such anchors will be made, as known in the art, from body tissue compatible, non-corrosive material, preferably titanium. They will be placed in holes preformed in the patient's bone by the known techniques whereby minimal stress and trauma are caused. They will then remain implanted for a healing period of from three to nine months, and during this healing period the will be subjected to minimal stress. During this period a cap e.g. of nylon, will be placed to fill or close the socket 13.

Each of the anchors 1 shown in FIGS. 1, 2, or 5, has a head 11 surmounting a cylindrical shank portion 12, which extends into a screw threaded portion 14, the threads of which are preferably self tapping threads.

At the foot of the anchor of the embodiment of FIG. 1 there is a sole 16 having the shape of a shallow dome. The inner ends of the holes preformed in the bone to receive the anchor are left verY slightly undersized, as shown at 18 in FIG. 1, and as shown in FIG. 1a the domed sole 16 has lateral flats 17 which afford a measure preventing rotation when engaged with bone; while the edges of the domed sole 16 are sharp semi-discs which are adapted to interlock with the bone, when the anchor is lightly screwed down to fill the preformed hole during initial placement. Immediately above the domed sole 16 there is an annular recess 19 which receives bone chippings produced when the anchor is screwed home.

The diameter of the shank portion 12 is the same diameter as the outside diameter of the threads of portion 14. If then the anchor is screwed into a preformed hole which is deliberately slightly undersized, the diameter of the inside diameter of the threads the screw threads will "bite" the bone and the following shank portion will fully occupy the region scored by the threads after they have passed by.

One or more transverse through perforations are formed in the screw threaded portion 14 it being intended that the bone should reform and enter into these perforations during the healing period after initial implantation. During this period the bone will reform in the recess 19 and around the screw threads. The anchors will not be modified by the surgeon. They will be available in a range of 14 lengths 7 mms to 20 mms and in a range of diameters of say 2.5 mms to 6 mms.

A single through perforation 7 exists in the anchor 1 of the embodiment of FIG. 5, and as shown in FIG. 5a, the ends 7a of the perforation are formed sharp so that they can cut into bone. The rounded base 8 may have flats at its sides to assist keying against rotation.

Figure 6A:
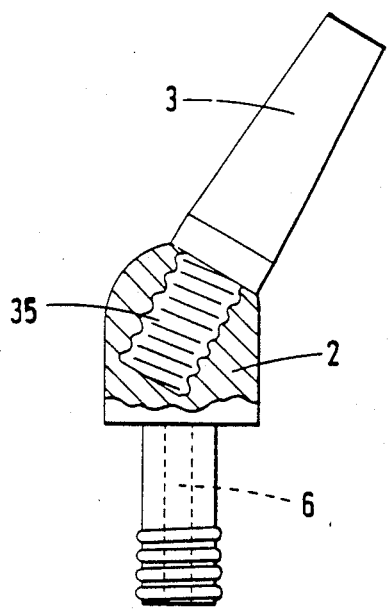
FIGS. 6A-6D show an intermediate transmucosal spacer member surmounted by a post in alternative configurations, any one of which may be substituted for the spacer member of FIG. 5.
Figure 6B:
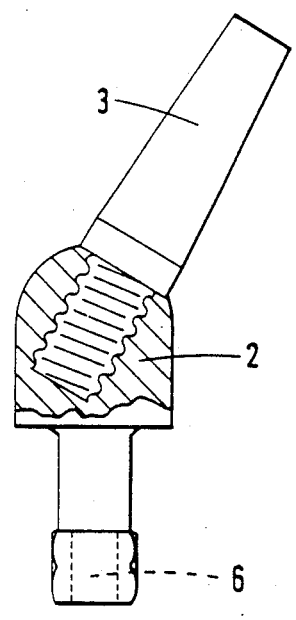
Figure 6C:
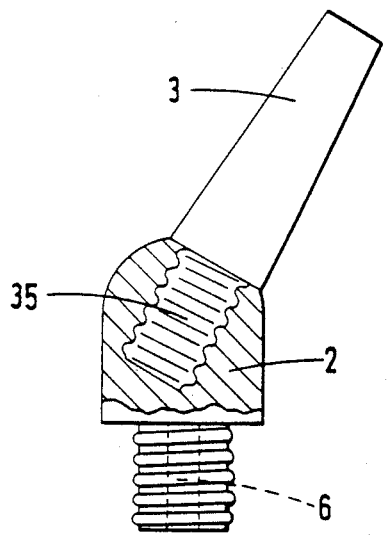
Figure 6D:
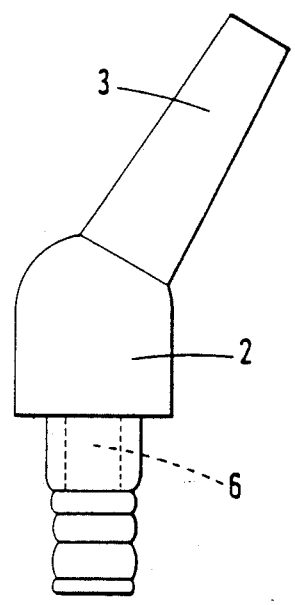

The interengaging keying means between the plug 23 of trancmucosal spacer member 2 and the socket 13 of the anchor 1 may as shown in FIGS. 6B And 6D, be by positive engagement of corresponding splined or hexagonally formed parts of the lengths of the plug and socket, this positive engagement being achieved by relative axial movement of the parts after adjustment by relative rotation and prior to final fixing achieved with the aid of bonding or cementing.

Some existing analogous systems and devices require that multiple implants be made in such a way that their anchors are parallel at the surgical stage so inhibiting the angle of placement; and some other systems involve bending of parts in situ and after implantation, this risking possible fracture as stress lines are set up in the material of the parts so bent. The system and devices as now proposed provide one answer to the problem of aligning one implant with another implant or with adjacent teeth. Each anchor can be implanted in such a location as to afford optimal bone support without fear that it cannot be aligned above the mucosa. The attachments secured to the anchor can be changed at a later date by way of adjustment or as required according to the needs of the patient.

By the means described above there is achieved a combination of anchor implanted for osseo integration by the known and perfected surgical techniques, together with a new intermediate transmucosal spacer member for mounting a prosthesis using an interposed post, the combination being such that the transmucosal spacer member and the post mounted thereon when installed, constitute in effect an axially offset extension of the anchor. The angle of the offset of the post axis is variable and selectable, and the offset extension is adjustable as to its orientation in azimuth relative to the implanted anchor, prior to permanent or semi-permanent fixing, by relative rotation of parts at the interconnection between the offset extension and the head of the anchor. And this is acheived without any bending or other deformation of parts in situ, and without delay being occasioned by need to make a permanent transmucosal spacer member from a temporary model, as was required with some known systems and devices as above referred to.

I claim:

1. For mounting a dental prosthesis including a single crown and a mounted set of crowns,
   the combination of firstly, a post (3) for mounting the prosthesis, secondly, an intermediate transmucosal spacer member (2) which in turn mounts the post, and thirdly, an anchor (1) adapted to be implanted in bone for osseo integration therewith, said anchor including a head end (11) to which the intermediate transmucosal spacer member (2) is connected;
   the combination of these three elements wherein the intermediate transmucosal spacer member (2) and the head end (11) of the anchor (1) form a junction where connected, and at the region of their junction have the same external shape and size so that they interfit with a minimal void at their junction,
   and the intermediate transmucosal spacer member (2) having an end remote from the anchor (1) and thereat a head which is hemispherically domed, said spacer member head having a threaded hole (25) therein with an outwardly opening mouth, said post having a screw threaded stud (35) threaded into said hole,
   said anchor having a major axis,
   said hole (25) having an axis which extends at a predetermined angle from the major axis of the anchor (1),
   the post (3), when screw threadedly connected to the intermediate transmucosal spacer member (2), extending away from the hemispherically domed head of the intermediate transmucosal spacer member (2), in a direction which is offset, at said predetermined angle, from the major axis of the anchor (1).

2. The combination of claim 1 wherein the head end (11) of the anchor (1) has a generally cylindrical external shape, and wherein the transmucosal spacer member (2) has a corresponding external cylindrical shape in its region which adjoins the anchor (1) when the two are connected together.

3. The combination of claim 1 wherein the head end (11) of the anchor (1) has a generally cylindrical external shape, and wherein the transmucosal spacer member (2) is tapered in its region where it adjoins the anchor (1) when the two are connected together.

4. The combination of any one of claims 1, or 2 or 3, including a socket (13) extending axially into the head end (11) of the anchor, the intermediate transmucosal spacer member with its domed head (22) having a plug (23) comprising an elongated spigot received in said socket (13); the plug and the socket having corresponding respective keying means, the orientation of the intermediate transmucosal spacer member, in azimuth relative to the implanted anchor, being adjustable by rotation of the plug in the socket with a bonding agent between the plug and the socket clamping the plug (23) in the socket (13) and interacting with the keying means of these two parts, so as thereafter to prevent relative rotation between the two parts.

5. The combination of claim 4 wherein the keying means comprises formations extending axially of the external surfaces of the plug (23) and of the socket (13).

6. The combination of claim 5 wherein the external surface of at least one of said plug and said socket is formed with a screw-thread in addition to said keying means.

7. The combination of claim 4 wherein the plug and the socket have substantially the same axial length.

8. The combination of claim 4 wherein the external surface over at least part of the length of both of said plug (23) and said socket (13) is formed hexagonal, said hexagonal lengths interengaging when the plug is fully inserted in the socket.

9. The combination of claim 1 wherein said intermediate transmucosal spacer member (2) has a major axis, the said threaded hole (25) in the domed head (22) of the intermediate transmucosal spacer member (2) having an axis which is offset and inclined at a predetermined angle (37) to the major axis of the intermediate transmucosal spacer member, and from the major axis of the anchor (1) when the intermediate transmucosal spacer member is attached thereto, of between 5° and 45°.

10. The combination of claim 9 including a set of such intermediate transmucosal spacer members with holes (25) of different offset angles (37), respectively differing by 5° and forming part or all of the series 5°, 10°, 15°, 20°, 25°, 30°, 35°, 40° and 45°.

11. The combination of claim 10 including as part of the set of such intermediate transmucosal spacer members, at least one intermediate transmucosal spacer member (2) with an axially aligned hole (25).

12. The combination of claim 1 wherein the intermediate transmucosal spacer member (2) and the post (3) secured thereto are both of the same titanium alloy material.

13. The combination of claim 1 wherein the intermediate transmucosal spacer member (2) has such length such that when installed connected to the head (11) of the anchor (10), the domed head (22) of the intermediate transmucosal spacer member is approximately level with the surface of a patient's mucosa or gum tissue.

14. For mounting a dental prosthesis including a single crown and a mounted set of crowns,
a set of components comprising:
a first group of components each comprising a post (3), each for mounting a prosthesis;
a second group of components each comprising an intermediate transmucosal spacer member (2), each for mounting a said post (3);
and a third group of components each comprising an anchor (1) adapted to be implanted in bone for osseo integration therewith, each said anchor including a head end (11) to which an intermediate transmucosal spacer member (2) is connectable;
the set wherein each said intermediate transmucosal spacer member (2) and the head end (11) of each said anchor (1) form a junction when connected, and at the region of their junction have the same external shape and size so that they interfit with a minimal void at their junction,
and each said intermediate transmucosal spacer member (2) having an end remote from the anchor-connecting end and thereat a head which is hemispherically domed, each said spacer member having a threaded hole (25) therein with an outwardly opening mouth, each said post having a screw threaded stud (35) for threading into a spacer member hole,
each said anchor having a major axis,
said hole (25) of each said intermediate transmucosal spacer member (2) when connected to the head of a said anchor, having an axis which is offset at a predetermined angle from the major axis of the anchor (1), and a said post (3), when then connected by means of its screw threaded stud (35) to the offset hole (25) of a said intermediate transmucosal spacer member (2), extending away from the hemispherically domed head of that intermediate transmucosal spacer member (2), in a direction which is offset, at said predetermined angle, from the major axis of the anchor (1);
the said second group of components including a plurality of such intermediate transmucosal spacer members (2), each with holes (25) of different offset angles (37), respectively differing by multiples of 5° and forming part or all of the series 5° 10° 15° 20° 25° 30° 35° 40° and 45°.

15. The set of claim 14 wherein the head end (11) of each said anchor (1) has a generally cylindrical external shape, and wherein a said transmucosal spacer member (2) has a corresponding external cylindrical shape, of the same external size, in its region which adjoins the head (11) of the anchor (1) when the two are connected together.

16. The set of claim 14 wherein the head end (11) of each said anchor (1) has a generally cylindrical external shape, and wherein a said transmucosal spacer member (2) is tapered in its region where it adjoins the anchor (1) when the two are connected together.

17. The set of any one of claims 14, or 15 or 16 including a socket (13) axially into the head end (11) of each said anchors, each said intermediate transmucosal spacer member with its domed head (22) having a plug comprising an elongated spigot insertable into a socket (13), the plugs and the sockets having corresponding respective keying means, the orientation of an intermediate transmucosal spacer member, in azimuth relative to an implanted anchor, being adjustable by rotation of the plug in the socket and the respective keying means becoming interengaged by application of a bonding agent between the plug and the socket to clamp the plug (23) in the socket (13) and to interact with the keying means of these two parts, so as thereafter to prevent relative rotation between the two parts.

18. The set of 17 wherein the external surface over at least part of the length of both of one of said plugs and one of said sockets being formed hexagonal, said hexagonal lengths interengaging when the plug is fully inserted in the socket.

19. In a device for the mounting of a dental prosthesis, a post for mounting the prosthesis, an intermediate transmucosal spacer member which in turn mounts the post, and an anchor adapted to be implanted in bone for osseo integration therewith, said anchor having a longitudinal axis and including a head at one end to which the intermediate transmucosal spacer member is connected;
the combination of these elements wherein the intermediate transmucosal spacer member is joined to the head end of the anchor by a plug and socket connection comprising an elongated plug on said intermediate transmucosal spacer member and a socket extending axially into said anchor, said intermediate transmucosal spacer member having a head opposed to said plug, the post for mounting the prosthesis when mounted to the intermediate transmucosal spacer member, extending away from the intermediate transmucosal spacer member in a direction which is offset at a predetermined angle from the axis of the anchor, the orientation in azimuth relative to the anchor, of said intermediate transmucosal spacer member with said post mounted to it, being adjustable as and when the plug and socket connection between the intermediate transmucosal spacer member and the anchor is being made, after which the transmucosal spacer member is held secured to the anchor by bonding or cementing means so that its orientation in azimuth relative to the anchor is therefore substantially fixed, the plug and the socket having corresponding respective keying means whereby, the orientation of the intermediate transmucosal spacer member azimuth relative to the implanted anchor having been adjusted by rotation of the plug in the socket, the application of the bonding or cementing means between the plug and the socket is effective both to clamp the plug in the socket and to interact with the keying means of these two parts to prevent relative rotation between the plug and the socket.

20. The combination of claim 19 wherein the keying means comprises formations extending axially of the external surfaces of the plug and of the socket.

21. The combination of claim 20 wherein the plug and socket connection includes a screw-thread surface between said socket in addition to said keying means.

22. The combination of any one of claims 19, 20 or 21 wherein the plug and the socket have substantially the same axial length.

23. The combination of claim 20 wherein said formations extend over at least part of the lengths of said plug and said socket and are positioned to interengage by relative axial movement of the plug and socket after adjustment of the intermediate transmucosal spacer member azimuth by rotation of the plug in the socket.

24. The combination of claim 23 wherein said formation on said plug extends inwardly from the end of said plug for a part of the length thereof.

25. The combination of claim 24 wherein said formations comprise hexagonal configurations on the plug and in the socket.

26. The combination of claim 19 wherein the head of the intermediate transmucosal spacer member is domed with one screw-threaded hole formed therein, and the post for mounting the prosthesis has as its foot a threaded stud which is screwed into the hole in the intermediate transmucosal spacer member.

27. The combination of claim 26 wherein the said screw-threaded hole in the domed head of the intermediate transmucosal spacer member has an axis which is offset and inclined at a predetermined angle to the major axis of the intermediate transmucosal spacer member and from the axis of the anchor when the intermediate transmucosal spacer member is attached thereof, said predetermined angle being between 5° and 45°.

28. The combination of claim 27 including a set of such intermediate transmucosal spacer members for selection by the surgeon, each with the screw-threaded hole therein being of a different offset angle, respectively differing by 5°; such as in the series 5°, 10°, 15° . . . 35° 40° 45°.

29. The combination of claim 28 wherein, as part of the set of such intermediate transmucosal spacer members available to the surgeon, at least one intermediate transmucosal spacer member has an axially aligned, non-offset, screw-threaded hole therein.

30. The combination of claim 19 wherein the intermediate transmucosal spacer member and the post secured thereto are both of the same material.

31. The combination of claim 19 wherein the plug having been inserted into the socket, the intermediate transmucosal spacer member and the anchor have the same external cylindrical shape and diameter, a cylindrical body portion of the intermediate transmucosal spacer member having sufficient length such that when installed the head of the intermediate transmucosal spacer member will be approximately level with the surface of the patient's mucosa or gum tissue.

* * * * *